(12) United States Patent
Murray (10) Patent No.: US 12,005,238 B2
(45) Date of Patent: Jun. 11, 2024

(54) IMPACT RESISTANT AND TAMPER EVIDENT SYSTEM FOR PREFILLED SYRINGE

(71) Applicant: FRESENIUS KABI USA, LLC, Lake Zurich, IL (US)

(72) Inventor: Christopher J. Murray, Lake Zurich, IL (US)

(73) Assignee: FRESENIUS KABI USA, LLC, Lake Zurich, IL (US)

( * ) Notice: Subject to any disclaimer, the term of this patent is extended or adjusted under 35 U.S.C. 154(b) by 748 days.

(21) Appl. No.: 16/949,226

(22) Filed: Oct. 20, 2020

(65) Prior Publication Data
US 2022/0118190 A1    Apr. 21, 2022

(51) Int. Cl.
*A61M 5/31* (2006.01)
*A61M 5/315* (2006.01)

(52) U.S. Cl.
CPC ...... *A61M 5/31501* (2013.01); *A61M 5/3129* (2013.01); *A61M 5/31571* (2013.01); *A61M 2005/3101* (2013.01); *A61M 2205/02* (2013.01)

(58) Field of Classification Search
CPC .......... A61M 5/31501; A61M 5/31505; A61M 5/3129; A61M 5/31571; A61M 2005/3101; A61M 2005/31508; A61M 5/002; A61M 5/1785
See application file for complete search history.

(56) References Cited

U.S. PATENT DOCUMENTS

| | | |
|---|---|---|
| 3,342,319 A | 9/1967 | Faulseit |
| 4,174,238 A | 11/1979 | Fowles et al. |
| 4,353,869 A | 10/1982 | Guth |
| 4,667,837 A | 5/1987 | Vitello et al. |
| 4,979,616 A | 12/1990 | Clanton |
| 5,135,496 A | 8/1992 | Vetter et al. |
| 5,322,515 A | 6/1994 | Karas et al. |
| 5,328,474 A | 7/1994 | Raines |
| 5,519,931 A | 5/1996 | Reich |
| 5,554,134 A | 9/1996 | Bonnichsen |
| 5,615,772 A | 4/1997 | Naganuma |
| 5,649,622 A | 7/1997 | Hollister |

(Continued)

FOREIGN PATENT DOCUMENTS

| | | |
|---|---|---|
| EP | 0716860 A2 | 6/1996 |
| EP | 0766975 A1 | 4/1997 |

(Continued)

*Primary Examiner* — Robert J Utama
*Assistant Examiner* — Justin L Zamory
(74) *Attorney, Agent, or Firm* — Blank Rome LLP (57) ABSTRACT

A syringe assembly and methods of producing the syringe assembly are described. The syringe assembly may include a syringe body, a plunger rod, a barrel cover, and a tamper evident device. The syringe body has a chamber configured to receive a material. The plunger rod moves within the chamber to dispense the material. The barrel cover covers the syringe body. The backstop is attached to the barrel cover to prevent a portion of the plunger rod from moving proximally through the backstop. The tamper evident device includes a tamper evident cap covering a distal portion of the syringe body, a collar attached to the barrel cover, and a frangible connection between the tamper evident cap and the collar.

23 Claims, 8 Drawing Sheets

(56) References Cited

U.S. PATENT DOCUMENTS

| | | | |
|---|---|---|---|
| 5,658,254 A | 8/1997 | Reichenbach et al. |
| 5,680,945 A | 10/1997 | Sander et al. |
| 5,785,691 A | 7/1998 | Vetter et al. |
| 5,833,653 A | 11/1998 | Vetter et al. |
| 5,843,047 A | 12/1998 | Pyrozyk et al. |
| 5,851,200 A | 12/1998 | Higashikawa et al. |
| 5,876,379 A | 3/1999 | Beauvais et al. |
| 5,944,699 A | 8/1999 | Barrelle et al. |
| 5,989,227 A | 11/1999 | Vetter et al. |
| 6,073,759 A | 6/2000 | Amborne et al. |
| 6,193,688 B1 | 2/2001 | Balestracci et al. |
| 6,196,998 B1 | 3/2001 | Jansen et al. |
| 6,330,959 B1 | 12/2001 | Dark |
| 6,368,305 B1 | 4/2002 | Dutton |
| 6,432,088 B1 | 8/2002 | Huang et al. |
| 6,485,460 B2 | 11/2002 | Eakins et al. |
| 6,491,665 B1 | 12/2002 | Vetter et al. |
| 6,520,935 B1 | 2/2003 | Jansen et al. |
| 6,585,691 B1 | 7/2003 | Vitello |
| 6,726,652 B2 | 4/2004 | Eakins et al. |
| 6,846,303 B2 | 1/2005 | Eakins et al. |
| 6,929,126 B1 | 8/2005 | Herbert |
| 6,942,643 B2 | 9/2005 | Eakins et al. |
| 7,144,238 B2 | 12/2006 | Chao |
| 7,374,555 B2 | 5/2008 | Heinz et al. |
| 7,488,307 B2 | 2/2009 | Rimlinger et al. |
| 7,632,244 B2 | 12/2009 | Buehler et al. |
| 7,806,861 B2 | 10/2010 | Witowski |
| 8,075,535 B2 | 12/2011 | Carrel et al. |
| 8,348,895 B1 | 1/2013 | Vitello |
| 8,591,462 B1 | 11/2013 | Vitello |
| 8,784,377 B2 | 7/2014 | Ranalletta et al. |
| 9,144,465 B2 | 9/2015 | Hunkeler et al. |
| 9,174,010 B2 | 11/2015 | Vedrine |
| 9,333,146 B2 | 5/2016 | Perot et al. |
| 9,333,288 B2 | 5/2016 | Hilliard et al. |
| 9,480,801 B2 | 11/2016 | Schiller et al. |
| 9,579,463 B2 | 2/2017 | Okihara |
| 9,758,281 B2 | 9/2017 | Glaser et al. |
| 9,821,152 B1 | 11/2017 | Vitello et al. |
| 9,925,340 B2 | 3/2018 | Glocker |
| 9,937,301 B2 | 4/2018 | Ward |
| 10,039,887 B2 | 8/2018 | Sundquist et al. |
| 10,052,437 B2 | 8/2018 | Duinat et al. |
| 10,064,998 B2 | 9/2018 | Duinat et al. |
| 10,124,122 B2 | 11/2018 | Zenker |
| 10,792,431 B2 | 10/2020 | Duinat et al. |
| 2001/0003150 A1 | 6/2001 | Imbert |
| 2003/0014018 A1 | 1/2003 | Giambattista et al. |
| 2004/0133169 A1 | 7/2004 | Heinz et al. |
| 2004/0225258 A1 | 11/2004 | Balestracci |
| 2008/0300550 A1 | 12/2008 | Schiller et al. |
| 2009/0209939 A1* | 8/2009 | Verespej ........... A61M 5/326 604/82 |
| 2009/0283493 A1 | 11/2009 | Witowski |
| 2011/0015578 A1 | 1/2011 | Lowke |
| 2011/0087173 A1 | 4/2011 | Sibbitt, Jr. et al. |
| 2012/0111368 A1 | 5/2012 | Rahimy et al. |
| 2013/0081974 A1 | 4/2013 | Hilliard et al. |
| 2013/0082057 A1 | 4/2013 | Schiff et al. |
| 2013/0338604 A1 | 12/2013 | Roedle |
| 2014/0078854 A1 | 3/2014 | Head et al. |
| 2014/0262883 A1 | 9/2014 | Devouassoux et al. |
| 2015/0343155 A1 | 12/2015 | Zenker et al. |
| 2016/0001015 A1* | 1/2016 | Kücük ............ A61M 5/5086 604/110 |
| 2016/0151584 A1 | 6/2016 | Deleuil et al. |
| 2016/0200484 A1 | 7/2016 | Cosman |
| 2018/0273261 A1 | 9/2018 | Qiu |
| 2019/0099557 A1 | 4/2019 | Potdar et al. |
| 2019/0161229 A1 | 5/2019 | Mase |
| 2020/0238023 A1 | 7/2020 | Murray et al. |

FOREIGN PATENT DOCUMENTS

| | | |
|---|---|---|
| EP | 1410819 A1 | 4/2004 |
| EP | 2826508 A1 | 1/2015 |
| EP | 2900301 B1 | 9/2016 |
| EP | 3381492 A1 | 10/2018 |
| WO | 2001023017 A2 | 4/2001 |
| WO | 2006018626 A1 | 2/2006 |
| WO | 2014049097 A1 | 4/2014 |
| WO | 2018024624 A1 | 2/2018 |

* cited by examiner

IMPACT RESISTANT AND TAMPER EVIDENT SYSTEM FOR PREFILLED SYRINGE

TECHNICAL FIELD

This disclosure relates generally to devices and methods of manufacturing and using syringes containing medical materials, and more particularly relates to an impact resistant and tamper evident system for a prefilled syringe.

BACKGROUND

Syringe assemblies are used to hold, transport, and deliver materials. For example, syringes are often utilized in medical environments to administer one or more medicinal components to a patient. Syringes can be delivered to a user empty or prefilled. Empty syringes are intended to be filled by the user from a vial or other container, whereas prefilled syringes are supplied to the user with a material (e.g., medicament or diluent) provided therein by a manufacturer. When prefilled, the syringes are often filled at a manufacturer site and shipped to the user ready-to-use.

However, the manufacturers have a number of difficulties in effectively producing and shipping the prefilled syringes. One issue is that the syringes can be fragile and often break during the handling of shipping. Another issue is that the manufacturer needs to ensure that the material in the syringe has not been tampered with after filling. Yet another issue is that the internal fluid pressure of the prefilled syringe can lead to the plunger rod popping out of the syringe during shipping.

Therefore, there is a need for improved syringe assemblies and methods of assembling prefilled syringes.

SUMMARY

The foregoing needs are met by the various embodiments of syringe assemblies and methods of preparing syringe assemblies disclosed.

One aspect of the present disclosure is directed to a syringe assembly having a syringe body, a plunger rod, a barrel cover, a backstop, and a tamper evident device. The syringe body may have a chamber configured to receive a material. The plunger rod may be configured to move within the chamber to dispense the material. The barrel cover may cover the syringe body. The backstop may be attached to the barrel cover to prevent a portion of the plunger rod from moving proximally through the backstop. The tamper evident device may include a tamper evident cap covering a distal portion of the syringe body, a collar attached to the barrel cover, and a frangible connection between the tamper evident cap and the collar.

Another aspect of the present disclosure is directed to a syringe assembly having the syringe body, the plunger rod, the barrel cover, the backstop, the tamper evident assembly, and an anti-rotation member. The syringe body may define the chamber configured to receive a material. The plunger rod may be configured to slidably move within the chamber to dispense the material. The barrel cover may receive the syringe body. The backstop may be attached to the barrel cover to prevent the portion of the plunger rod from passing through the backstop. The tamper evident assembly may include the tamper evident cap covering the distal portion of the syringe body, the collar attached to the barrel cover, and the frangible connection between the tamper evident cap and the collar. The anti-rotation member may be configured to prevent rotation of the collar during breakage of the frangible connection.

Yet another aspect is directed to a method for producing a syringe assembly for administering a material. The method may include attaching the tamper evident assembly to the distal end of the barrel cover, inserting the syringe body into the barrel cover, and attaching the backstop to the syringe body to prevent the portion of the plunger rod from moving proximally through the backstop. The tamper evident assembly may be attached by connecting the collar to the barrel cover, wherein the tamper evident assembly has the frangible connection between the tamper evident cap and the collar.

In some embodiments, the barrel cover may be translucent and/or transparent. In some embodiments, the barrel cover may have a proximal opening and a distal opening. In some embodiments, the collar may include a ridge that snaps into a groove on a distal portion of the barrel cover. In some embodiments, the backstop may be configured to snap onto a proximal portion of the barrel cover. In some embodiments, the barrel cover may include a flange, and the backstop may include a slot configured to receive the flange. In some embodiments, the backstop and the flange may form a continuous outer surface with the flange received in the slot. In some embodiments, the backstop may include first and second backstop members. In some embodiments, the first and second backstop members may be semi-circumferential. In some embodiments, the plunger rod may include a stopper at a distal end, and the backstop may be configured to contact the stopper to prevent the stopper from passing through the backstop. In some embodiments, the backstop may be configured to contact the plunger rod to prevent the plunger rod from moving proximally through the backstop. In some embodiments, the syringe body may be made of glass or plastic. In some embodiments, the syringe body may include a flange at a proximal portion, and the barrel cover may include a plurality of ridges supporting the flange of the syringe body. In some embodiments, a syringe cap may cover a distal portion of the syringe body. In some embodiments, the anti-rotation member may include a plurality of teeth or grooves on an outer surface of the barrel cover. In some embodiments, the anti-rotation member may include a plurality of teeth or grooves on an inner surface of the collar. In some embodiments, the anti-rotation member may include an adhesive or an abrasive surface.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In the drawings.

Aspects of the disclosure will now be described in detail with reference to the drawings, wherein like reference numbers refer to like elements throughout, unless specified otherwise.

DETAILED DESCRIPTION OF ILLUSTRATIVE EMBODIMENTS

An impact resistant and tamper evident system for a prefilled syringe, and method of assembling the system, are described. The system may provide a protective enclosure during shipping, handling, storage, and/or use of the prefilled syringe, without requiring secondary packaging. The system may have a barrel cover that protects the syringe body and is translucent and/or transparent to allow the clinician to view labels and/or graduation marks in or on the syringe body. The barrel cover may, additionally or alternatively, protect the material from environmental factors that may negatively impact biological stability of the material. The system may also have backstop members that snap on a proximal portion of the barrel cover to secure and prevent a plunger rod from being removed or fluid from being diverted through a plunger stopper. The system may further have a tamper evident device disposed over a distal tip of the syringe body and at a distal portion of the barrel cover. The tamper evident device may include a tamper evident cap removable from the distal tip of the syringe body by a user twisting and breaking frangible bridges. An anti-rotation feature on the barrel cover and/or tamper evident device may prevent rotation of the remaining portion of the tamper evident device during removal of the cap.

The impact resistant and tamper evident system of the present disclosure provides a number of advantageous features that benefit the manufacturer and user, as discussed herein. The system ensures protection of the syringe and filled material, while allowing the user to administer the material without removal of the syringe from the barrel cover. The system prevents the plunger rod from being removed from the syringe chamber ensuring containment of the material. The system mechanically protects the syringe during shipping by providing a protective cover and reducing movement of the syringe relative to the protective barrel cover. The system also allows the manufacturer and user to view the medicament and/or indicia in or on the syringe, while the syringe is protected by the barrel cover. Additional advantageous features of the impact resistant and tamper evident system are evident from the present disclosure.

FIGS. 1-8 illustrate exemplary embodiments of a syringe system 10 containing a material 20, such as a liquid medicament. The syringe system 10 may have a flange 12 and include a syringe 100, a barrel cover 200, a tamper evidence device 300, and a backstop 400.

Figure 2:
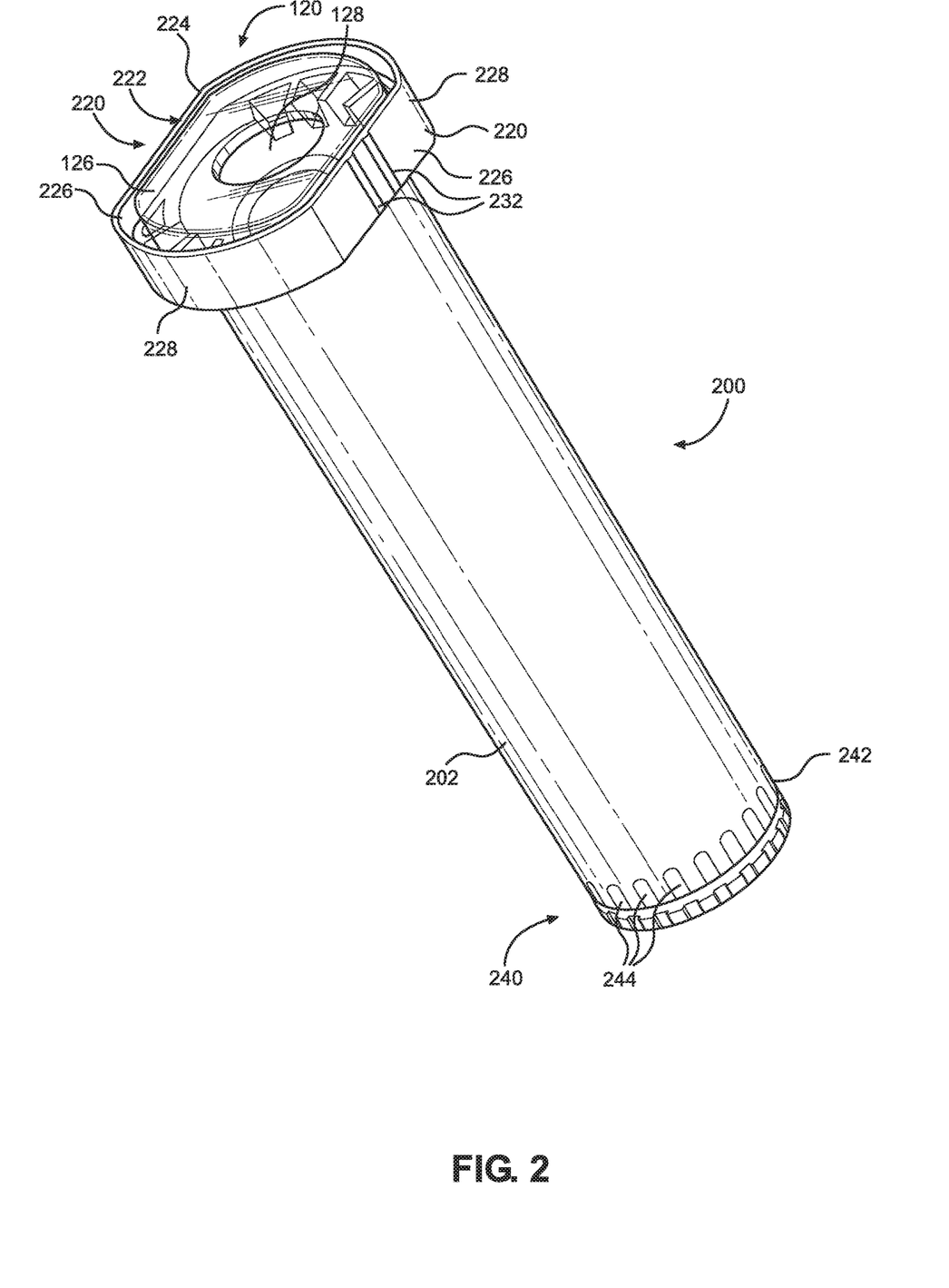
FIG. 2 illustrates an isometric view of a barrel cover containing a syringe body.
Figure 7:
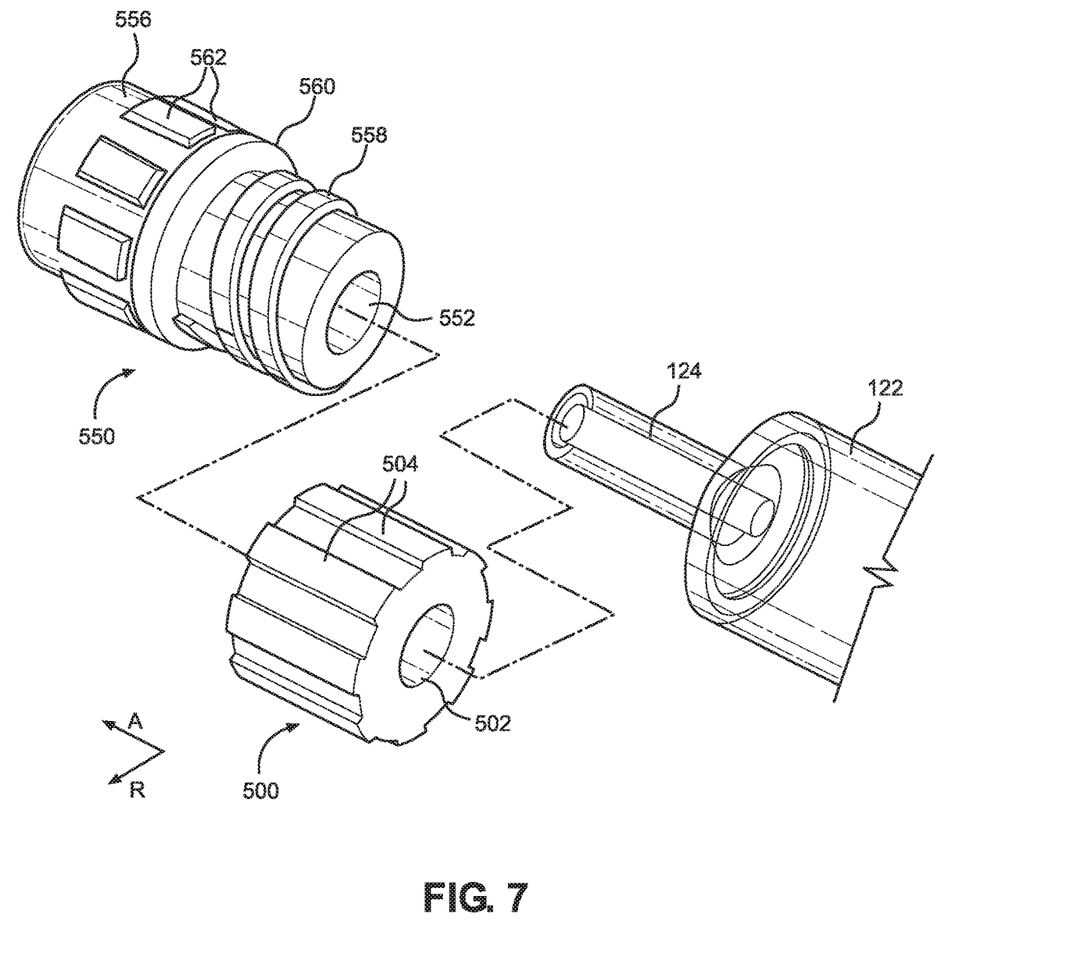
FIG. 7 illustrates an exploded view of a tip assembly.

The syringe 100 may include a syringe body 120 and a plunger rod 140. The syringe body 120 may have a syringe barrel 122 extending from a proximal end to a distal end along a longitudinal direction. The syringe body 120 may further have a tip 124 at the distal end (as illustrated in FIG. 7) and a flange 126 at the proximal end (as illustrated in FIG. 2). The syringe barrel 122 may be substantially cylindrical having an inner surface extending along the longitudinal direction to define a chamber 130. The chamber 130 may be configured to receive, store, and/or mix the material 20 for dispensing through a distal opening of the syringe tip 124. The syringe body 120 may have indicia 132 in and/or on an outer surface of the syringe barrel 122 providing data and/or information of the material 20, such as name, dose, expiration date, instructions, and/or recipient. The indicia 132 may, additionally or alternatively, include graduations providing measurements of the remaining amount of the material 20. The indicia 132 may, additionally or alternatively, include a marking representing data in machine-readable form, such as a linear barcode, radio frequency identification tag, and/or QR code. In some embodiments, the indicia 132 are provided on a label that is affixed to the outer surface of the syringe barrel 122.

The syringe tip 124 may include a connection interface for engagement with an external device (not shown), such as a syringe needle, a medical transport line, or a container. The syringe tip 124 may be tapered and/or further have a Luer connection. The syringe flange 126 may extend radially outwards from the proximal end of the syringe body 120 to enable stability and handling of the syringe body 120. The syringe flange 126 may have a substantially oval shape with two flat, oppositely positioned sides and two arcuate, oppositely positioned sides (as illustrated FIG. 2). Alternatively, the syringe flange 126 may have a different shape, such as a substantially circular shape. The syringe flange 126 may have a proximal opening 128 sized to receive the plunger rod 140 and defining a proximal end of the chamber 130.

The plunger rod 140 may have a plunger stopper 160 at a distal end to define the proximal-most extent to which the material 20 can fill the chamber 130. The plunger stopper 160 may have an enlarged, substantially cylindrical body. The plunger stopper 160 may be made of a flexible elastomeric material (e.g., rubber) and generally conform to the shape of the chamber 130 to prevent leakage of the material 20 proximally out of the chamber 130. As the plunger stopper 160 moves distally through the chamber 130, the plunger stopper 160 may push the material 20 out of the chamber 130 through the syringe tip 124. Similarly, as the plunger stopper 160 moves proximally through the chamber 130, the plunger stopper 160 may create a vacuum to draw the material 20 into the chamber 130 through the syringe tip 124. The plunger rod 140 may include a plurality of vanes 142 extending radially and longitudinally along the length of the plunger rod 140. The plunger rod 140 may include four vanes 142, where the vanes 142 are arranged circumferentially spaced apart 90 degrees forming a substantially plus-shaped orientation. The vanes 142 may function to provide stability and strength to the plunger rod 140, while minimizing the cross-sectional footprint of the plunger rod 140 to reduce material requirements for the plunger rod 140, thus reducing overall weight of the syringe assembly.

The syringe body 120 and/or plunger rod 140 may be made of glass or a translucent and/or transparent plastic material, such as polyethylene terephthalate (PET), polypropylene (PP), polycarbonate (PC), or other material. However, the invention may be particularly suitable for embodiments where the syringe body 120 is made of glass, which provides a stable container reducing biological degradation of the material 20 and extending the expiration.

Figure 1:
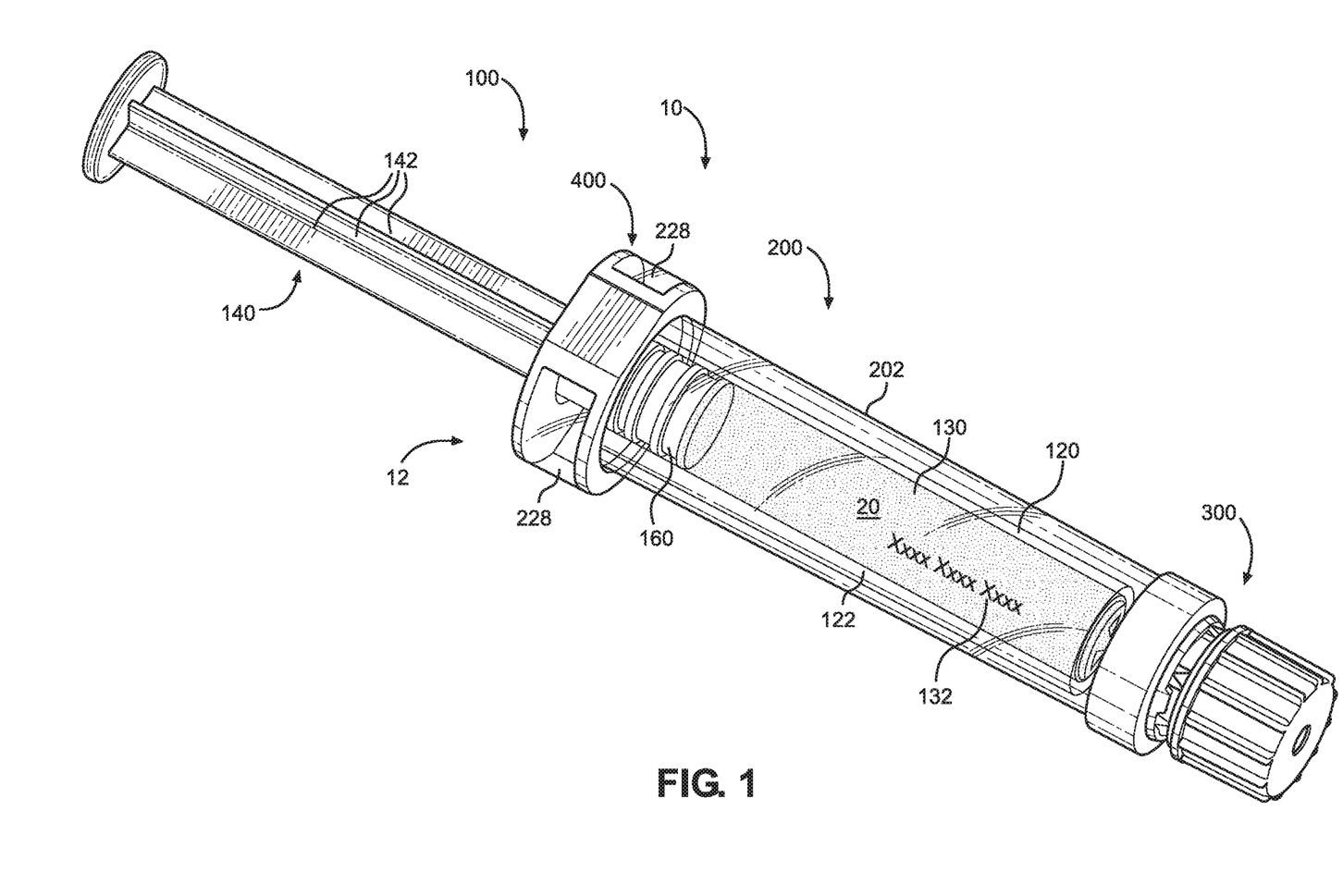
FIG. 1 illustrates an isometric view of an embodiment of a syringe assembly.
Figure 3:
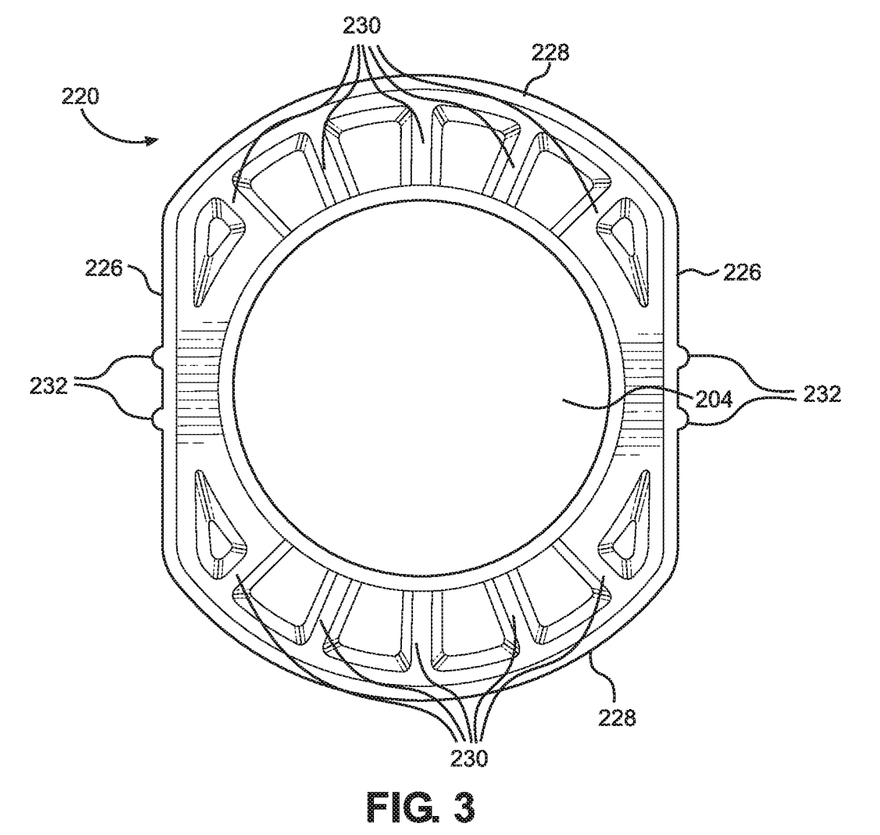
FIG. 3 illustrates a proximal view of the barrel cover.

As further illustrated in FIGS. 1-3, the syringe body 120 may be received in the barrel cover 200 to provide a protective enclosure without requiring secondary packaging. The barrel cover 200 may include a tubular barrel 202 extending from a proximal end to a distal end along a longitudinal direction. The barrel cover 200 may have a proximal opening 204 to receive the syringe body 120 and a distal opening 206 to receive the syringe tip 124 when the syringe body 120 is inserted. The distal opening 206 may allow the syringe 100 to dispense the material 20 while inside the barrel cover 200 to ensure protection.

The barrel cover 200 may be made of an impact resistant, translucent and/or transparent plastic material, such as polyethylene terephthalate (PET), polypropylene (PP), polycarbonate (PC), or other material. The barrel cover 200 made of plastic may provide mechanical protection to the syringe body 120 against external forces during shipping, handling, storage, and/or use of the syringe 100, especially useful when the syringe body 120 is made of glass. At least a portion of the barrel cover 200 (e.g., the entire length of the tubular barrel 202) may form a viewing window that allows the user to see the indicia 132 in and/or on the outer surface of the syringe barrel 122. Thus, the barrel cover 200 may provide visual access to essential data/information of the syringe 100, while maintaining protection of the syringe 100. The barrel cover 200 may also provide visual access to the contents of the syringe 100, to determine the volume and/or status of the material 20 remaining in the syringe 100. In some embodiments, the color, transparency and/or other attributes of the barrel cover 200 may be selected based on, for example, a characteristic, such as the UV sensitivity, of the material 20 contained inside the syringe. Additionally, the color and/or other attributes of the barrel cover 200 may be selected based on a desired color coding scheme of the syringe packaging and/or other labeling considerations. In some embodiments, the barrel cover 200 may have indicia in and/or on an outer surface of the barrel cover 200 providing data and/or information of the material 20, such as name, dose, expiration date, instructions, and/or recipient in human and/or machine-readable form. In certain embodiments, the indicia are provided on a label that is affixed to the outer surface of the barrel cover 200.

The barrel cover 200 may further have a flange 220 at the proximal end and an anti-rotation feature 240 at the distal end. The anti-rotation feature 240 may include an annular groove 242 and a plurality of teeth or grooves 244, according to some embodiments. The teeth or grooves 244 may be longitudinally interrupted by the annular groove 242, such that two sets of teeth or grooves 244 are formed on opposing longitudinal sides of the annular groove 242. The cover flange 220 may have a recess 222 defined by a circumferential wall 224 and configured to receive the syringe flange 126 of the syringe barrel 122. The cover flange 220 may have a substantially oval shape including first and second opposing substantially flat wall portions 226 and first and second opposing arcuate wall portions 228. Alternatively, the cover flange 220 may have a different shape, such as a substantially circular shape. The cover flange 220 may be slightly larger than the syringe flange 126 and have a shape that substantially matches the shape of the syringe flange 126, such that the circumferential wall 224 surrounds the syringe flange 126. The cover flange 220 may include a plurality of ridges 230 extending proximally and radially around/from the proximal opening 204 and positioned below the proximal end of the circumferential wall 224. The ridges 230 may be configured to support the syringe flange 126 by providing stability and an improved seat to the syringe flange 126. The ridges 230 may also improve manufacturability, for example, by reducing deformation and ease of ejection of the syringe body 120 from a molding tool. The cover flange 220 may additionally include ridges and/or grooves 232 configured to secure the backstop members 402.

Figure 4:
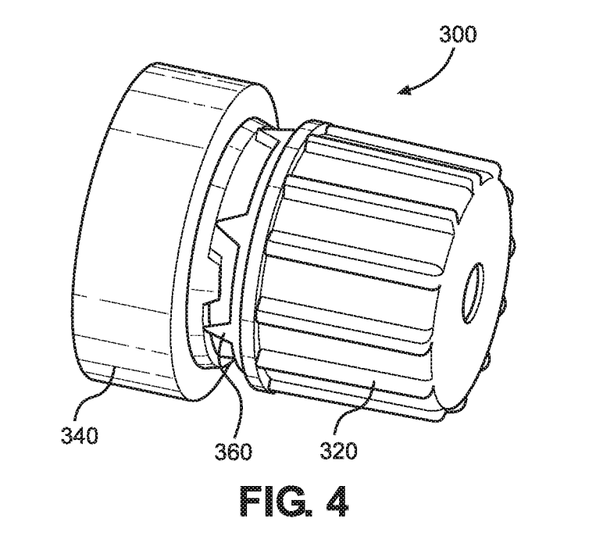
FIG. 4 illustrates an isometric view of a tamper evident device.
Figure 5A:
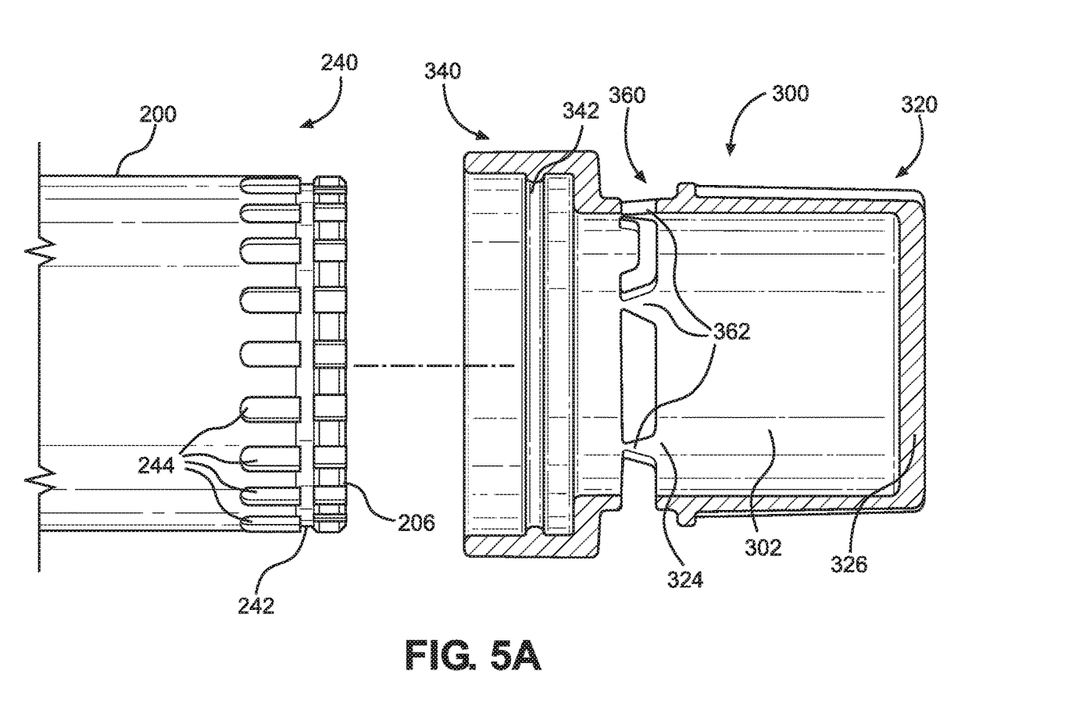
FIGS. 5A-C illustrate exploded views of embodiments of the tamper evident device and the barrel cover.
Figure 5B:
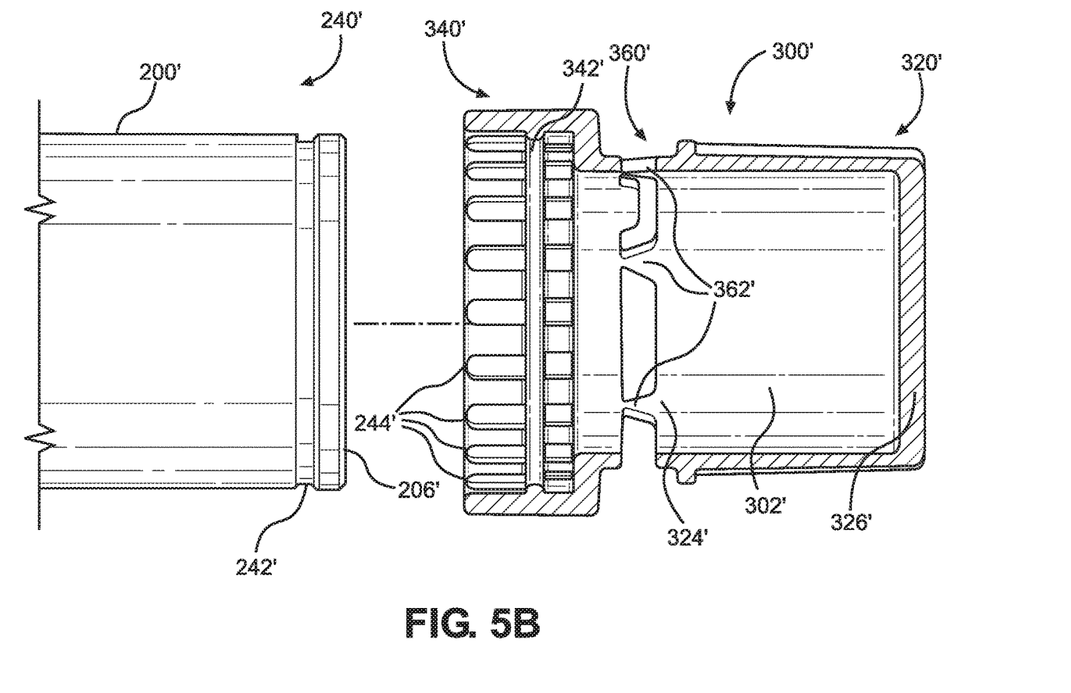
Figure 5C:
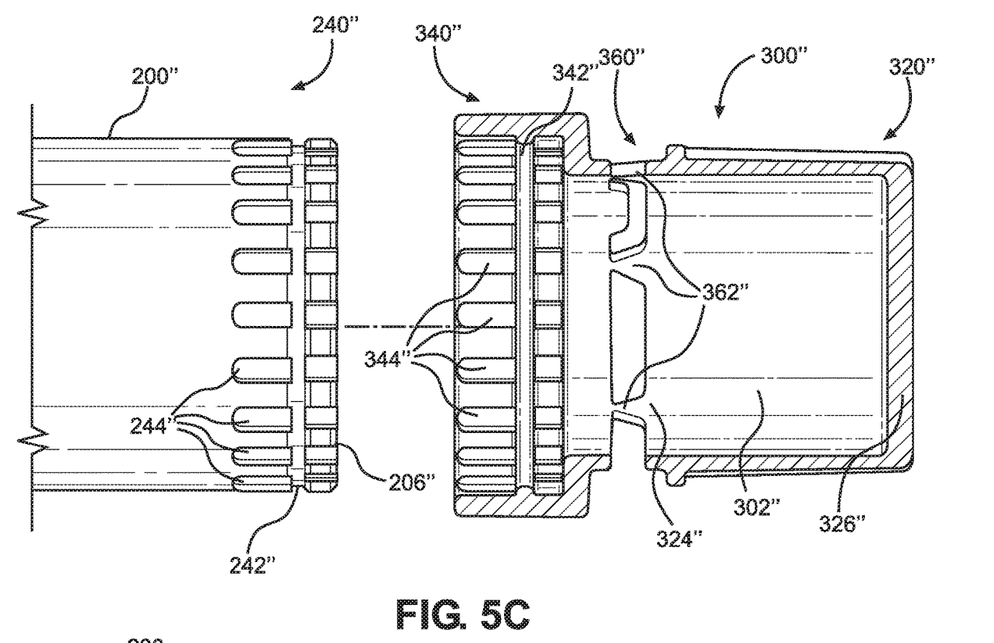
Figure 6:
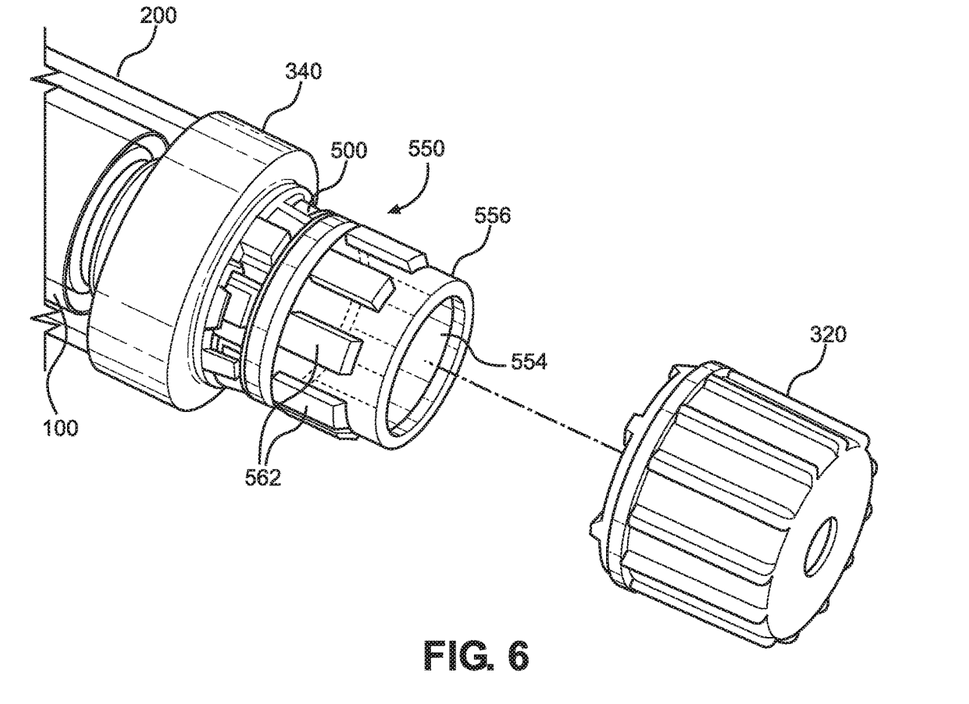
FIG. 6 illustrates an isometric view of a released configuration of the tamper evident device.

As further illustrated in FIGS. 4-6, the tamper evident device 300 may include a cap 320, a collar 340, and a frangible connection 360, each defining a longitudinal passage 302. The tamper evident device 300 may ensure that the material 20 is not improperly accessed after filling, during shipping, handling, and/or storage.

The tamper evident cap 320 may be a substantially hollow cylinder and define an outer surface and an inner surface. The inner surface may define the passage 302 configured to receive the syringe tip 124 and/or a tip cap 550. The tamper evident cap 320 may have an open proximal end 324 and a closed distal end 326, where the passage 302 extends from the open proximal end 324 along the longitudinal direction and terminates within the main body at a location proximal to the distal end 326. However, in other embodiments, the distal end of the tamper evident cap 320 may be open or partially closed.

The collar 340 may be initially attached to the cap 320 and substantially surround a distal portion of the barrel cover 200. The collar 340 may include an annular rib 342 in an inner surface configured to snap into the annular groove 242 on the outer surface of the barrel cover 200 during assembly to longitudinally fix the collar 340 and cap 320. The snap connection between the collar 340 and barrel cover 200 may provide a tactile and/or audible indication of a proper connection.

The frangible connection 360 may include a plurality of frangible bridges 362 spaced around the circumference of the tamper evident device 300. The frangible bridges 362 may releasably connect the tamper evident cap 320 and the collar 340, such that when the frangible connection 360 is broken, the tamper evident cap 320 may be removed from the syringe tip 124. Each of the frangible bridges 362 may embody a thin portion of the tamper evident device 300 that tapers inwards in width as it extends proximally. However, the frangible bridges 362 may be alternatively configured, such as having a constant width. Further, the frangible bridges 362 may be equidistantly spaced about the circumference of the tamper evident device 300. The frangible connection 360 may define a plurality of gaps between the frangible bridges 362, which allow the tamper evident device 300 to be broken at the frangible connection 360 by the user providing a substantial rotational or twisting force to the tamper evident cap 320 relative to the collar 340.

FIGS. 5A-C illustrate various embodiments of the anti-rotation feature 240 provided between the inner surface of the collar 340 and the outer surface of the barrel cover 200. The various embodiments of the anti-rotation feature 240 may prevent or reduce rotation of the collar 340 as the user rotates or twists the cap 320 to expose the distal portion of the syringe body 120 and/or tip cap 550. As illustrated in FIG. 5A, the anti-rotation feature 240 may include the plurality of teeth or grooves 244 extending longitudinally and radially outward from the distal portion of the barrel cover 200, and the inner surface of the collar 340 may have no corresponding teeth or grooves. When the collar 340 is connected around the barrel cover 200, the teeth or grooves 244 may form an interference fit within the inner surface of the collar 340 to prevent relative rotation of the collar 340 during release of the tamper evident cap 320. The teeth or grooves 244 may be longitudinally interrupted by the annular groove 242, such that two sets of teeth or grooves 244 are formed on opposing longitudinal sides of the annular groove 242. In some embodiments, as illustrated in FIG. 5B, the inner surface of the collar 340' may include a plurality of teeth or grooves 344', and the outer surface of the barrel cover 200' may have no corresponding teeth or grooves. The teeth or grooves 344' may similarly form an interference fit with the outer surface of the barrel cover 200' to prevent relative rotation of the collar 340' during release of the tamper evident cap 320'. The teeth or grooves 344' may be longitudinally interrupted by the annular rib 342', such that two sets of teeth or grooves 344' are formed on opposing longitudinal sides of the annular rib 342'. In some embodiments, as illustrated in FIG. 5C, the anti-rotation feature 240" may include a plurality of teeth or grooves 244" on the outer surface of the barrel cover 200" and a plurality of teeth or grooves 344" on the inner surface of the collar 340". The corresponding teeth and/or grooves 244", 344" may interlock to prevent rotation of the collar 340" during rotation of the cap 320" during breakage of the frangible connection 360". The various embodiments of the anti-rotation feature 240, 240', 240" may, additionally or alternatively, include a sonic weld, adhesive, frictional surfaces, gripping material, etc. between the collar 340 and the barrel cover 200. In some embodiments, the anti-rotation feature 240 may include a film (not shown, replacing the collar 340) adhered over the barrel cover 200 to provide the frangible connection. In other embodiments, the collar 340 of the tamper evident device 300 may be integrated into the distal end of the barrel cover 200, e.g., as a singly molded component, such that an additional anti-rotation feature 240 is not needed to prevent relative rotation of the collar 340 during release of the tamper evident cap 320.

As further illustrated in FIGS. 6-7, the syringe assembly may include a tip assembly having a tip connector 500 and the tip cap 550 to seal the syringe 100 after filling. The tip connector 500 and the tip cap 550 may be received on the distal portion of the syringe 100, such that a proximal end of the tip connector 500 is received in the barrel cover 200. The tip connector 500 may extend distally out of the distal opening of the barrel cover 200 to expose the tip cap 550 for removal when the syringe 100 is received in the barrel cover 200. The tip cap 550 may be engaged to a distal end of the tip connector 500 and be received in the tamper evident cap 320. In some embodiments, the syringe assembly does not contain a tip connector, and the inner surface of the tip cap 550 is configured to engage with an external surface of the syringe tip 124, e.g., by way of an interference fit (not shown).

The tip connector 500 may be a separate component and be configured to receive the syringe tip 124 during assembly. The tip connector 500 may include a tubular body having a lumen 502 configured to receive the syringe tip 124. The tip connector 500 may be made of a flexible material to allow for radial expansion under fluid pressure applied by the syringe 100. The tip connector 500 may have a plurality of ribs 504 arranged circumferentially around an outer surface. The tip connector 500 may further have internal threads (not shown) on an inner surface to engage an outer surface of the tip cap 550.

The tip cap 550 may seal the syringe tip 124 to prevent the material 20 from leaking after the chamber 130 is filled. The tip cap 550 may have a tubular body defining a lumen 552 extending through an open proximal end to a distal wall 554 of a closed distal end 556. Outer threads 558 on an outer surface of the tip cap 550 may be configured to rotationally engage the inner threads of the tip connector 500, as the lumen 552 receives the syringe tip 124. The syringe tip 124 may extend through the lumen 552 until the syringe tip 124 contacts a proximal inner surface of the distal wall 554 of the closed distal end 556 in a sealed configuration. The contact between the syringe tip 124 and the close distal end 556 may generate an audible and/or tactile indication to the user that the syringe 100 is sealed. The tip cap 550 may additionally include a radially enlarged portion 560 configured to contact a distal surface of the tip connector 500 to provide a stop for the rotation of the tip cap 550 relative to the tip connector 500. The enlarged portion 560 may extend entirely or partially around the perimeter of the tip cap 550 and may extend to the distal end 556. The tip cap 550 may include a textured surface embodied by a plurality of ribs 562 on the enlarged portion 560 to facilitate twisting and rotation of the tip cap 550 relative to the tip connector 500. Upon removal of the tamper evident cap 320 from the collar 340, the syringe 100 may remain sealed until the tip cap 550 is removed from the tip connector 500 prior to use.

Figure 8:
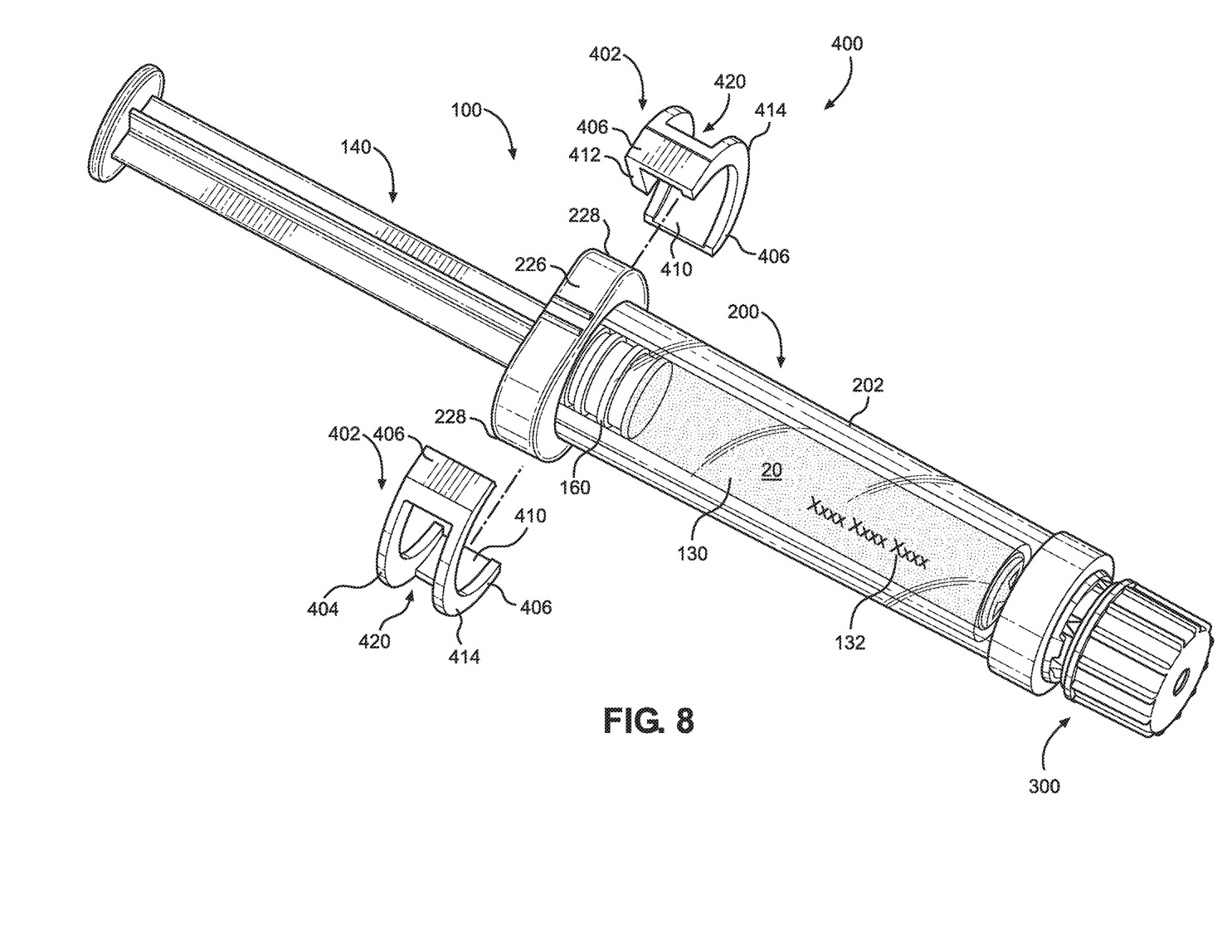
FIG. 8 illustrates a partially exploded view of the syringe assembly.

As further illustrated in FIG. 8, the backstop 400 may be releasably attached to a proximal portion of the barrel cover 200 to prevent the plunger rod 140 from being removed after the syringe 100 is filled with the material 20.

The backstop 400 may include at least two backstop members 402 releasably attachable to the proximal portion of the barrel cover 200. For example, the backstop 400 may include first and second backstop members 402, each having a slot 410 configured to snap onto the cover flange 220 and to prevent a portion of the plunger rod 140 from passing therethrough. The backstop members 402 may be separate components such that the backstop members 402 may be applied to the cover flange 220 independently. The first and second backstop members 402 may be identical, semi-circumferential pieces. The first and second backstop member 402 may be oriented 180 degrees from each other when assembled to collectively form the backstop 400. The backstop members 402 may be formed of a resiliently flexible material configured to snap onto the flange 220. For example, the cover flange 220 may include ridges and/or grooves 232 configured to engage and secure the backstop member 402. The backstop members 402 may each substantially match half of the shape of the cover flange 220. For example, the backstop members 402 may each have at least one arcuate portion 404 corresponding to the arcuate wall portion 228 of the flange 220, and at least one flat portion 406 corresponding to the substantially flat wall portions 226 of the flange 220. Although the backstop members 402 are illustrated in FIG. 8 having one arcuate portion 404 and two flat portions 406, the backstop members 402 may alternatively have one flat portion 406 and two arcuate portions 404 to fit over the cover flange 220 in a transverse configuration (not shown). In other embodiments, the backstop members 402 are semicircular. In some embodiments, the backstop members 402 may, additionally or alternatively, not be separate from each but be pivotably joined by a hinge member and/or be securable to each other on the cover flange 220 with a latch member when assembled to the cover flange 220 (not shown). The arcuate portion 404 may include an opening 420 that receives the arcuate wall portions 228 of the cover flange 220 therethrough to expose the arcuate wall portion 228 through each of the backstop members 402. Thus, the backstop 400 and the cover flange 220 may form a substantially continuous radial outer surface when the cover flange 220 is received in the backstop members 402. When assembled, the arcuate wall portions 228 of the cover flange 220 and the arcuate portion 404 of the backstop members 402 may form continuous outer arcuate surfaces, and the flat portions 406 of the backstop members 402 may join to form continuous outer flat surfaces. The continuous outer arcuate and flat surfaces may join to form a continuous perimeter surface of the flange 12 of the syringe system 10, as illustrated in FIG. 1. In other embodiments, the backstop members 402 do not contain an opening such that the arcuate wall portions 228 of the cover flange 220 are not exposed when the backstop 400 is assembled onto the barrel cover 200. In such embodiments, the backstop members 402 form a continuous perimeter surface of the flange 12 of the syringe system 10 (not shown).

The backstop 400 may prevent a portion of the plunger rod 140 (e.g., the plunger stopper 160) from moving out of the chamber 130 after filling the syringe 100 with the material 20. The backstop 400 may define a proximal opening and a distal opening having different dimensions and/or shapes. For example, the backstop members 402 may each have a proximal rim 412 collectively defining the proximal opening and a distal rim 414 collectively defining the distal opening. The slot 410 may be defined between the proximal rim 412 and the distal rim 414. The proximal rim 412 of each of the backstop members 402 may be larger or protrude further inward than the the distal rim 414. Thus, the proximal opening of the backstop 400 may be smaller than the proximal opening 128 of the syringe 100 to effectively reduce the size of the proximal opening of the syringe 100 when the backstop 400 is attached to the barrel cover 200. Therefore, the proximal rim 412 of the backstop members 402 may be configured to contact an enlarged portion of the plunger rod 140 or the plunger stopper 160 to prevent removal from the chamber 130. For example, the plunger stopper 160 may have a width larger than the proximal opening preventing removal of the plunger rod 140 proximally from the chamber 130 during shipping, handling, storage, and/or use. In some embodiments, the enlarged portion of the plunger rod 140 may be a flange that extends radially from the plunger rod body (not shown). The flange may have a substantially round cross section, but may have various other shapes depending on desired materials and manufacturing processes. In other embodiments, the enlarged portion of the plunger rod 140 may be one or more rectangular, triangular, or elliptical projections extending radially from the plunger rod body. The flange or projection may be disposed in any desired location along the length of the plunger rod 140. In some embodiments, the enlarged portion of the plunger rod 140 may be a midpoint along the length of the plunger rod 140 (not shown). In other embodiments, the enlarged portion may be at the distal end of the plunger rod 140 adjacent to the plunger stopper 160. However, the plurality of vanes 142 of the plunger rod 140 may have a width less than the enlarged portion and the proximal opening of the backstop 400 allowing passage of the plurality of vanes 142 through the proximal opening of the backstop 400, for example, during administration of the material 20. The distal rims 414 may be sized to correspond with and receive an outer surface of the barrel cover 200 when the backstop members 402 are assembled to the flange 220. The backstop 400 may also protect the syringe 100 by securing the syringe 100 to the barrel cover 200 and reducing relative movement. For example, the syringe flange 126 may be immovably secured between the ridges 230 of the cover flange 220 and the proximal rim 412 when the backstop 400 is received in the barrel cover 200. The securement may prevent damage to the syringe body 120 from relative movement with the barrel cover 200.

Figure 9:
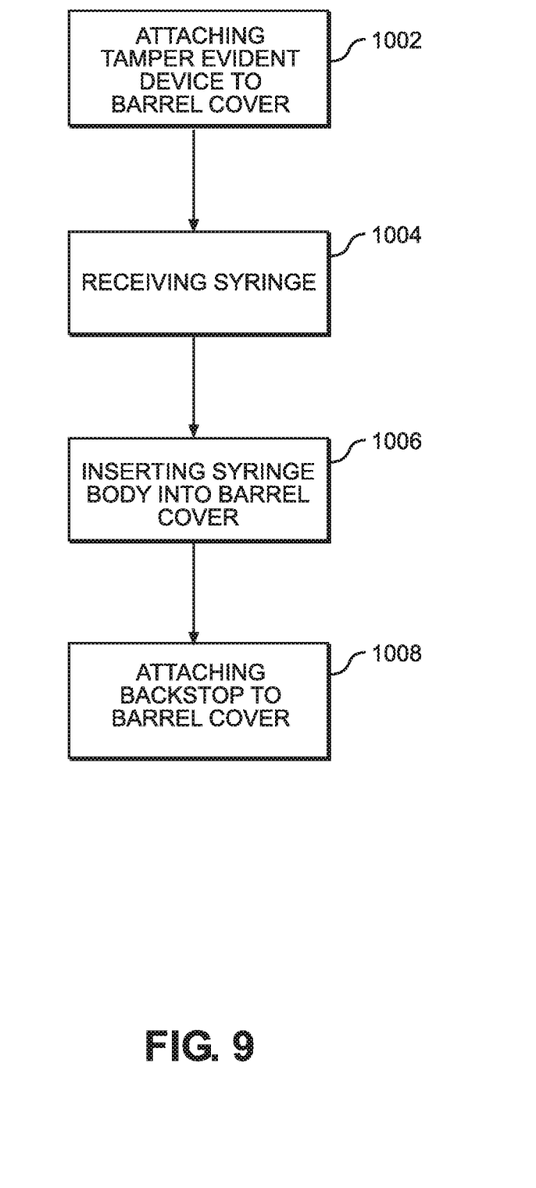
FIG. 9 illustrates a flow chart of a method of producing the syringe assembly.

Now referring to FIG. 9, a method 1000 of preparing the syringe assembly will be described. Method 1000 may begin with step 1002, wherein the tamper evident device 300 may be attached to the distal portion of the barrel cover 200. The annular rib 342 on the collar 340 may be receive in the annular groove 242 of the barrel cover 200. In step 1004, the syringe 100 is received, where the syringe 100 may include the syringe body 120 having the syringe tip 124 and the proximal opening 128. As discussed above, the syringe body 120 may define a chamber 130 extending along the longitudinal direction between the syringe tip 124 and the proximal opening 128. Preferably, the chamber has been filled with a material 20 and the plunger stopper 160 and plunger rod 140 are positioned within the chamber 130 when the syringe 100 is received. In step 1006, the syringe body 120 may be inserted into the proximal opening of the barrel cover 200, such that the syringe flange 126 is received in the cover flange 220 and the tip cap 550 extends out of a distal opening of the barrel cover 200 and is received in the cap 320.

In step 1008, the backstop 400 may be attached to the proximal portion of the barrel cover 200. For example, the backstop 400 may include first and second backstop members 402 configured to snap on opposing sides of the cover flange 220. The backstop members 402 may include a proximal rim 412 that effectively narrows the proximal opening of the syringe 100, preventing withdrawal of the portion of the plunger rod 140 from the chamber 130. In some embodiments, step 1002 may be performed after step 1006 of inserting the syringe body 120 into the proximal opening of the barrel cover 200, or after the step 1008 of attaching the backstop 400 to the proximal portion of the barrel cover. In other embodiments, the barrel cover 200 and tamper evident device 300 are provided as a preassembled component. In certain embodiments, the barrel cover 200 and tamper evident device 300 may be provided as a singly molded component.

While systems and methods have been described in connection with the various embodiments of the various figures, it will be appreciated by those skilled in the art that changes could be made to the embodiments without departing from the broad inventive concept thereof. It is understood, therefore, that this disclosure is not limited to the particular embodiments disclosed, and it is intended to cover modifications within the spirit and scope of the present disclosure as defined by the claims.

What is claimed is:

1. A syringe assembly comprising:
   a syringe body having a chamber configured to receive a material;
   a plunger rod configured to move within the chamber to dispense the material;
   a barrel cover configured to receive the syringe body, the barrel cover extending from a proximal portion to a distal portion;
   a backstop configured to attach to the proximal portion of the barrel cover to prevent a portion of the plunger rod from moving proximally through the backstop; and
   a tamper evident assembly including:
      a collar positioned at the distal portion of the barrel cover, wherein the distal portion of the barrel cover comprises a first attachment feature and the collar comprises a second attachment feature configured to attach to the first attachment feature, and
      a tamper evident cap attached to the collar by a frangible connection between the tamper evident cap and the collar.

2. The syringe assembly of claim 1, wherein the barrel cover is translucent and/or transparent.

3. The syringe assembly of claim 1, wherein the first attachment feature of the barrel cover is a groove and the second attachment feature of the collar is a ridge that snaps into the groove.

4. The syringe assembly of claim 1, wherein the backstop is configured to snap onto the proximal portion of the barrel cover.

5. The syringe assembly of claim 1, wherein the proximal portion of the barrel cover comprises a flange, and the backstop has a slot configured to receive the flange.

6. The syringe assembly of claim 1, wherein the backstop includes first and second backstop members.

7. The syringe assembly of claim 6, wherein the first and second backstop members are semi-circumferential.

8. The syringe assembly of claim 1, wherein the plunger rod includes a stopper at a distal end of the plunger rod, and the backstop is configured to contact the stopper to prevent the stopper from passing through the backstop.

9. The syringe assembly of claim 1, wherein the backstop is configured to contact an enlarged portion of the plunger rod to prevent the plunger rod from moving proximally through the backstop.

10. The syringe assembly of claim 1, the syringe body comprises a flange at a proximal portion of the syringe body, and the barrel cover comprises a plurality of ridges supporting the flange of the syringe body.

11. The syringe assembly of claim 1, further comprising a syringe cap covering a distal portion of the syringe body, wherein the tamper evident cap covers the syringe cap.

12. A syringe assembly comprising:
a syringe body defining a chamber configured to receive a material;
a plunger rod configured to move within the chamber to dispense the material;
a barrel cover configured to receive the syringe body, the barrel cover extending from a proximal portion to a distal portion;
a backstop configured to attach to the proximal portion of the barrel cover to prevent a portion of the plunger rod from passing through the backstop;
a tamper evident assembly including:
a collar configured to attach to the distal portion of the barrel cover, and
a tamper evident cap attached to the collar by a frangible connection between the tamper evident cap and the collar; and
an anti-rotation member on the barrel cover or the collar, the anti-rotation member configured to prevent rotation of the collar relative to the barrel cover during breakage of the frangible connection.

13. The syringe assembly of claim 12, wherein the anti-rotation member includes a plurality of teeth or grooves on an outer surface of the barrel cover.

14. The syringe assembly of claim 12, wherein the anti-rotation member includes a plurality of teeth or grooves on an inner surface of the collar.

15. The syringe assembly of claim 12, wherein the anti-rotation member includes an adhesive or an abrasive surface.

16. A method of assembling a syringe assembly for administering a material, the method comprising:
attaching a tamper evident assembly to a distal portion of a barrel cover, the distal portion of the barrel cover comprising a first attachment feature, wherein the tamper evident assembly comprises a collar that comprises a second attachment feature that is configured to attach to the first attachment feature, and wherein the tamper evident assembly further comprises a tamper evident cap that is connected to the collar by a frangible connection between the tamper evident cap and the collar;
inserting a pre-filled syringe into the barrel cover, the pre-filled syringe comprising a flange and a plunger rod; and
attaching a backstop to a proximal end of the barrel cover and over the flange of the pre-filled syringe to prevent a portion of the plunger rod of the pre-filled syringe from moving proximally through the backstop.

17. The method of claim 16, wherein attaching the backstop includes attaching a first backstop member and a second backstop member.

18. A syringe assembly comprising:
a syringe body having a chamber configured to receive a material;
a plunger rod configured to move within the chamber to dispense the material;
a barrel cover configured to receive the syringe body, the barrel cover extending from a proximal portion to a distal portion;
a backstop configured to attach to the proximal portion of the barrel cover to prevent a portion of the plunger rod from moving proximally through the backstop;
a tamper evident assembly including:
a collar positioned at the distal portion of the barrel cover, and
a tamper evident cap attached to the collar by a frangible connection between the tamper evident cap and the collar; and
an anti-rotation member on the barrel cover or the collar, the anti-rotation member configured to prevent rotation of the collar relative to the barrel cover during breakage of the frangible connection.

19. The syringe assembly of claim 18, wherein the breakage of the frangible connection comprises rotation of the tamper evident cap relative to the collar.

20. The syringe assembly of claim 12, wherein the breakage of the frangible connection comprises rotation of the tamper evident cap relative to the collar.

21. A syringe assembly comprising:
a syringe body having a chamber configured to receive a material;
a plunger rod configured to move within the chamber to dispense the material;
a barrel cover configured to receive the syringe body, the barrel cover extending from a proximal portion to a distal portion, the barrel cover comprises a flange at the proximal portion of the barrel cover;
a backstop configured to attach to the proximal portion of the barrel cover to prevent a portion of the plunger rod from moving proximally through the backstop, the backstop having a slot configured to receive the flange of the barrel cover, the backstop and the flange forming a continuous outer surface with the flange received in the slot; and
a tamper evident assembly including:
a collar configured to attach to the distal portion of the barrel cover, and
a tamper evident cap attached to the collar by a frangible connection between the tamper evident cap and the collar.

22. The syringe assembly of claim 21, wherein the barrel cover is translucent and/or transparent.

23. The syringe assembly of claim 21, wherein:
the collar is configured to snap onto the distal portion of the barrel cover, and
the backstop is configured to snap onto the proximal portion of the barrel cover.

* * * * *